(12) United States Patent
Schrecongost

(10) Patent No.: US 8,752,213 B2
(45) Date of Patent: Jun. 17, 2014

(54) TOUCHSCREEN-ACTIVE PROTECTIVE COVERING FOR DIGIT AND METHOD OF USING SAME, AND DISPENSERS THEREFOR

(76) Inventor: Nancy W. Schrecongost, Leland, NC (US)

( * ) Notice: Subject to any disclaimer, the term of this patent is extended or adjusted under 35 U.S.C. 154(b) by 59 days.

(21) Appl. No.: 13/467,535

(22) Filed: May 9, 2012

(65) Prior Publication Data

US 2013/0117901 A1      May 16, 2013

(51) Int. Cl.
*A41D 13/08*     (2006.01)
*A61F 13/10*     (2006.01)

(52) U.S. Cl.
CPC ............ *A41D 13/087* (2013.01); *A61F 13/105* (2013.01)
USPC .............................................................. 2/21

(58) Field of Classification Search
CPC .. A41D 13/087; A61F 13/105; A61B 19/045; A61B 19/04
USPC .......... 2/21, 163, 168, 169, 16; 345/179, 173; 221/26, 33, 34, 47; 602/22, 30, 31, 57, 602/58, 61, 63; 206/390
See application file for complete search history.

(56) References Cited

U.S. PATENT DOCUMENTS

| | | | | |
|---|---|---|---|---|
| 2,654,111 A * | 10/1953 | Ready | .............. | 15/227 |
| 2,701,878 A * | 2/1955 | Davis | .................. | 2/21 |
| 3,263,681 A * | 8/1966 | Nechtow et al. | ................... | 2/21 |
| 3,348,541 A * | 10/1967 | Loebeck | ......................... | 602/58 |
| 4,733,410 A | 3/1988 | Glotkin | | |
| 6,243,868 B1 * | 6/2001 | Wanzenried | ......................... | 2/21 |
| 6,647,549 B2 * | 11/2003 | McDevitt et al. | .................. | 2/21 |
| 7,012,169 B2 | 3/2006 | McDevitt et al. | | |
| 2001/0001883 A1 | 5/2001 | Wanzenried | | |
| 2001/0002431 A1 * | 5/2001 | Gurley | ........................... | 602/61 |
| 2003/0050589 A1 | 3/2003 | McDevitt et al. | | |
| 2004/0083530 A1 | 5/2004 | LeVert et al. | | |
| 2006/0137070 A1 * | 6/2006 | Yang et al. | ......................... | 2/21 |
| 2008/0106521 A1 * | 5/2008 | Nave | ............................. | 345/173 |
| 2009/0013441 A1 | 1/2009 | Duffy | | |
| 2010/0088794 A1 | 4/2010 | Oradini, Sr. | | |
| 2011/0265245 A1 * | 11/2011 | Asiaghi | ............................. | 2/167 |
| 2011/0289654 A1 * | 12/2011 | Williams et al. | .................. | 2/167 |
| 2012/0000002 A1 * | 1/2012 | Prince et al. | ......................... | 2/21 |
| 2012/0188182 A1 * | 7/2012 | McKenna | ........................ | 345/173 |
| 2013/0076690 A1 * | 3/2013 | Vellanki | ........................ | 345/174 |

FOREIGN PATENT DOCUMENTS

| | | | |
|---|---|---|---|
| CA | 2526815 A1 * | 5/2007 | |
| CH | 705232 A1 * | 1/2013 | |
| DE | 102009042792 A1 * | 3/2011 | |
| GB | 2481456 A * | 12/2011 | |

* cited by examiner

*Primary Examiner* — Amy Vanatta
(74) *Attorney, Agent, or Firm* — Triangle Patents, PLLC

(57) ABSTRACT

Touchscreen-active protective coverings for single digit or finger of a human hand and methods of using same.

18 Claims, 5 Drawing Sheets

TOUCHSCREEN-ACTIVE PROTECTIVE COVERING FOR DIGIT AND METHOD OF USING SAME, AND DISPENSERS THEREFOR

BACKGROUND OF THE INVENTION

1. Field of the Invention

The present invention relates to protective coverings for human hands, and more particularly, to touchscreen-active protective coverings for single digit or finger of a human hand.

2. Description of the Prior Art

It is known in the relevant art to provide finger protective coverings, and devices for dispensing them. However, none provide for touchscreen activation by a finger when covered therewith.

By way of example, the following prior art documents illustrate state of the art at the time of the invention:

US Patent Application Publication No. 20100088794 for Finger covers and devices for dispensing finger covers, by inventor Orandini, describes a disposable finger protector and dispensing device, where the cover is made of impermeable and inexpensive material, such as laminated wax paper, vinyl, parchment paper, latex, or rubber, for preventing the finger from becoming dirty or soiled, specifically when handling sticky or greasy food, when handling faucets, door handles and flush handles in public restrooms; the dispenser contains a plurality of openings for covering more than one finger inserted into the device;

US Patent Application Publication No. 20090013441 for Fingertip cover, by inventor Duffy, describes a disposable fingertip cover adhesively applied to the pad of the fingertip, the cover composed of germ and virus impermeable material such as plastic, latex, rubber, or a biodegradable material (paper not mentioned), wherein the fingertip covers are individually packaged for ease of application, and may include antimicrobial ingredients; the fingertip cover intended use is on public surfaces that have the potential to transmit germs and diseases, such as ATM keypads, touchscreens, elevator buttons, public phones, money, and door handles; however, the materials indicated do not function for touchscreen activation;

US Patent Application Publication No. 2004008350 for Finger and palm protector for public use, by inventors LeVert, et al., describes a finger and palm protective shield to prevent the transfer of disease and viruses to the palm and digits of the user, the shield composed of plastic/polymer, conventional fabrics, highly absorbent paper fibrous materials, metal, leather, etc, wherein these materials may be impregnated with agents for destroying viruses, and may be disposable or reusable; the protector is intended to be used on public surfaces, but does not teach or suggest touchscreen applications.

SUMMARY OF THE INVENTION

The present invention relates to finger and hand protective coverings, and more particularly to touchscreen-enabled protective coverings that allow for graphic user interface and display interactivity while protecting the user from direct contact germ transmission.

It is an object of this invention to provide a protective covering for a human hand digit including a sheath having a closed end and an open end, wherein the sheath is sized to cover a single digit of a human hand, the sheath being constructed and configured to receive the single digit via the open end; and wherein the closed end is operable to activate a touchscreen of an interactive graphic user interface and a corresponding display upon contact therewith, thereby providing protection from contact-based transmission of germs while enabling touchscreen activation that is substantially similar to a direct digit contact with the touchscreen.

It is an object of this invention to provide methods for using the touchscreen-enabled protective covering described and claimed herein.

Yet another object of this invention is to provide a dispenser for providing the touchscreen-enabled protective covering described and claimed herein.

These and other aspects of the present invention will become apparent to those skilled in the art after a reading of the following description of the preferred embodiment when considered with the drawings, as they support the claimed invention.

DETAILED DESCRIPTION

Figure 1:
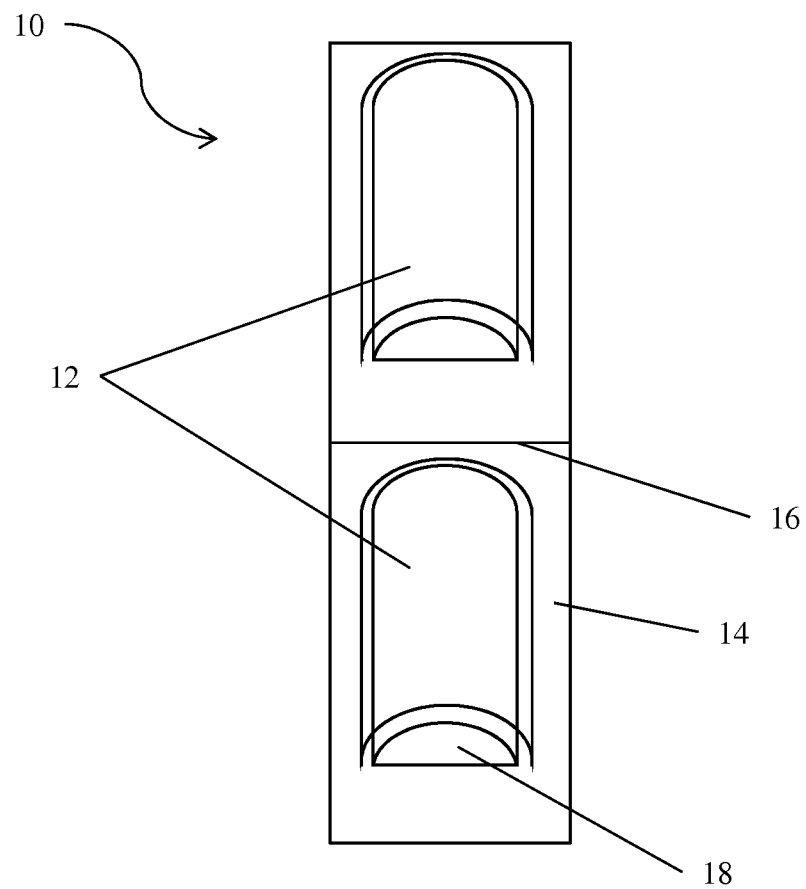
FIG. 1 is a top view diagram of one embodiment of the invention, showing a strip of two of the protective covers connected in a continuous strip.

Referring now to the drawings in general, the illustrations are for the purpose of describing a preferred embodiment of the invention and are not intended to limit the invention thereto.

Overall, the present invention, in one embodiment, provides a protective covering for a human hand digit including a sheath having a closed end and an open end, wherein the sheath is sized to cover a single digit of a human hand, the sheath being constructed and configured to receive the single digit via the open end; and wherein the closed end is operable to activate a touchscreen of an interactive graphic user interface and a corresponding display upon contact therewith, thereby providing protection from contact-based transmission of germs while enabling touchscreen activation that is substantially similar to a direct digit contact with the touchscreen.

In another embodiment of the present invention, dispenser (s) are provided for housing the touchscreen-activatable protective coverings, wherein they are selectively removable from the housing for use in providing protection from contact-based transmission of germs while enabling touchscreen activation that is substantially similar to a direct digit contact with the touchscreen.

The present invention provides protective covering for a human hand digit including: a sheath having a closed end and an open end, wherein the sheath is sized to cover a single digit of a human hand, the sheath being constructed and configured to receive the single digit via the open end; and wherein the closed end is operable to activate a touchscreen of an interactive graphic user interface and a corresponding display upon contact therewith, thereby providing protection from contact-based transmission of germs while enabling touchscreen activation that is substantially similar to a direct digit contact with the touchscreen. The sheath is formed of a non-porous, impermeable material that is disposable and biodegradable; more preferably, a non-woven material is used. In one embodiment, the present invention is formed from a lightweight cellulosic, preferably a paper product.

In one embodiment of the present invention, the sheath further includes an outer surface and an inner surface, and wherein at least one of the outer surface and inner surface is coated and/or impregnated with a sanitizing agent.

Also, preferably, the sheath is substantially cylindrical, and has a length between about 1.5 cm and about 5 cm; also, preferably, the sheath is substantially cylindrical and having a length between about 2.0 cm and about 4.5 cm; more preferably, the sheath is substantially cylindrical and having a length between about 2.5 cm and about 4.0 cm.

FIG. 1 is a top view diagram of one embodiment of the invention, generally described as 10, showing a strip of two of the protective covers 12 connected in a continuous strip. In one embodiment, the individual protective coverings are each arranged and removably attached to a presentation medium or support medium 14, wherein each individual protective finger covering is separated from others by a perforated, tearable, and/or breakable connecting line 16, as shown. The continuous strip provides presentation with the open end of the substantially cylindrical protective covering 18 facing downwardly or outwardly as depicted, to allow for a fingertip to be inserted into the open end. The open end is formed from two layers of the sheath presenting a three-dimensional concave opening as depicted in FIG. 1.

Figure 2:
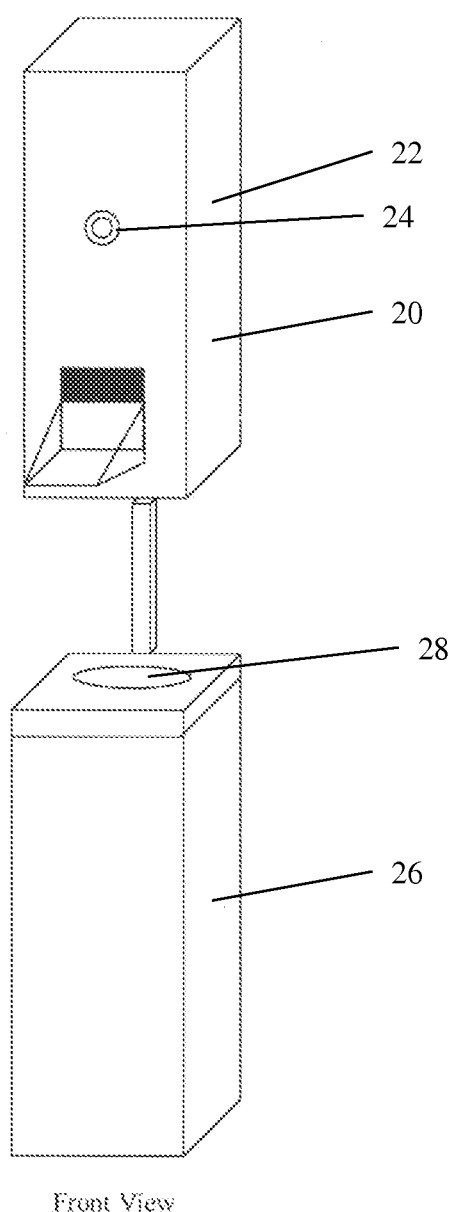
FIG. 2 is a perspective view diagram of another embodiment of the invention, including a dispenser for the protective covers of the present invention.

FIG. 2 is a perspective view diagram of another embodiment of the invention, including a dispenser 20 for the protective covers of the present invention. As illustrated, an automatic dispenser for removably containing and allowing for individual removal of at least one protective finger covering as set forth hereinabove, the dispenser includes a top housing 22 containing a multiplicity of unused protective finger coverings. In preferred embodiments of the present invention, the multiplicity of unused protective finger coverings are supplied in a continuous roll, wherein each individual protective finger covering is separated from others by a perforated, tearable, and/or breakable connecting line (shown in FIG. 1). Upon activation of a motion sensor 24 constructed and configured on a front side of the top housing, the dispenser automatically releases an individual protective finger covering through an opening in the top housing. For using each individual protective finger covering, the user places his/her finger in the protector opening end and removes it from the presentation medium with an upwardly lifting motion to loosen the protective finger covering from the presentation medium. In one embodiment, the removably secured protective finger covering is attached to the presentation medium (or surface) by heat-bonding. The user then having at least one protective finger covering over a corresponding fingertip and pad region of the finger, provides contact-based pressure on a touch screen of a display. After completing any and all touchscreen interaction for the display, the user removes the protective covering from the finger without contacting the exposed surface of the protector, and placing it in a disposal portion or lower portion 26 that includes a waste receptacle 28. The top housing and lower portion of the housing may be constructed of any suitable material, such as by way of example and not limitation, molded plastic material. While the dispenser housing is illustrated with corners, rounded edges may be used for safety, and such modifications are considered design optimization, and included within the scope of the present invention.

Figure 3:
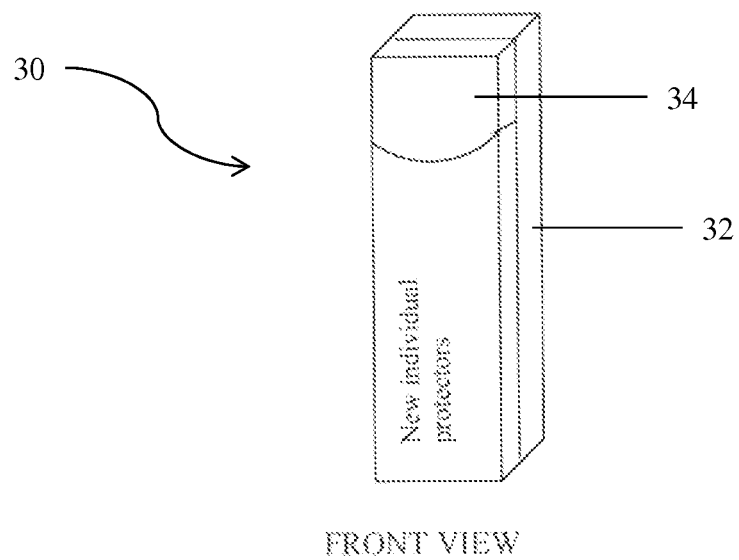
FIG. 3 is a front view diagram of another embodiment of the invention, including a kit or package for dispensing the protective covers of the present invention.
Figure 4:
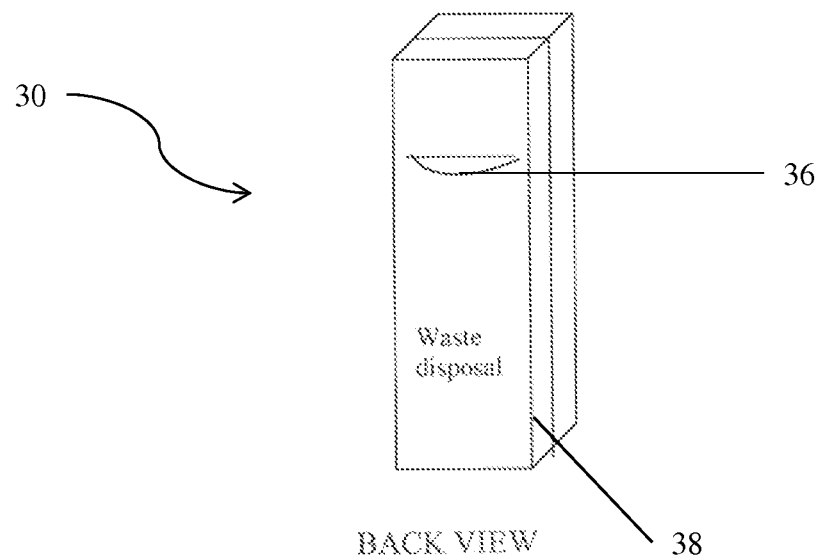
FIG. 4 is a back view diagram of the embodiment illustrated in FIG. 3.
Figure 5:
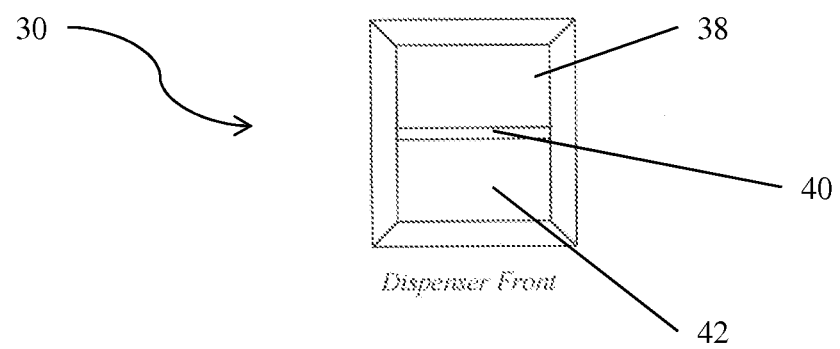
FIG. 5 is a top view diagram of the embodiment illustrated in FIG. 3.

In a series of related figures, FIGS. 3-5, a personal pocket pack dispenser, generally described as 30, for the protective finger coverings described hereinabove is shown. FIG. 3 is a front view diagram of an embodiment of the invention, including a kit or package for dispensing the protective covers of the present invention, wherein the individual finger protectors or protective finger covers are disposed inside the housing 32 shown. As illustrated, the housing includes a flip top 34 for opening the housing to access the protective finger covers contained within the housing. FIG. 4 is a back view diagram of the embodiment illustrated in FIG. 3, showing an opening or a slit 36 in the housing side. The opening is sized and constructed to receive used protective covers, allowing the covers to be forced into the opening, which provides access into a waste disposal section 38 of the housing, that is separated from the new, unused protective coverings by a divider 40, such as a cardboard separator (shown in FIG. 5). FIG. 5 is a top view diagram with a cross-sectional view of the embodiment illustrated in FIG. 3, illustrating the waste disposal section 38, and the section of the housing that is sized, constructed and configured for holding the new finger protectors 42. In one embodiment, the dispenser is constructed from a lightweight paper product, such as by way of example and not limitation, lightweight cardboard, preferably recycled paper product.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

What is claimed is:

1. A protective covering for a human hand digit comprising:
    a sheath having a closed end and an open end;
    wherein the sheath is sized to cover a single digit of a human hand, the sheath being constructed and configured to receive the single digit via the open end, and the sheath being removably positioned on a backing material;
    the sheath further including an outer surface and an inner surface, the outer surface and/or the inner surface coated and/or impregnated with a sanitizing agent;
    the backing material further including a perforated, tearable, and/or breakable connecting line;
    wherein the open end of the sheath is spaced apart from the perforated, tearable, and/or breakable connecting line, and the open end is formed from two layers of the sheath presenting a three-dimensional concave opening; and
    wherein the closed end of the sheath is operable to activate a touchscreen of an interactive graphic user interface and a corresponding display upon contact therewith;
    thereby providing protection from contact-based transmission of germs while enabling touchscreen activation that is substantially similar to a direct digit contact with the touchscreen.

2. The protective covering of claim 1, wherein the sheath is formed of a non-porous, impermeable material.

3. The protective covering of claim 1, wherein the sheath is formed of a non-porous, impermeable material that is disposable and biodegradable.

4. The protective covering of claim 1, wherein the sheath is formed of a non-woven material.

5. The protective covering of claim 1, wherein the sheath is formed of a lightweight cellulosic material.

6. The protective covering of claim 5, wherein the sheath is formed of paper.

7. The protective covering of claim 1, wherein the sheath is substantially cylindrical.

8. The protective covering of claim 1, wherein the sheath is substantially cylindrical and having a length between about 1.5 cm and about 5 cm.

9. The protective covering of claim 1, wherein the sheath is substantially cylindrical and having a length between about 2.0 cm and about 4.5 cm.

10. The protective covering of claim 1, wherein the sheath is substantially cylindrical and having a length between about 2.5 cm and about 4.0 cm.

11. A method for using a protective covering comprising the steps of: providing a protective covering according to claim 1, wherein the protective covering allows a user to activate a touchscreen by physical contact from the finger inserted in the open end.

12. A protective covering for a human hand digit comprising:
   a sheath having a closed end and an open end;
   wherein the sheath is sized to cover a single digit of a human hand, the sheath being constructed and configured to receive the single digit via the open end, and the sheath being removably positioned on a backing material;
   the backing material further including a perforated, tearable, and/or breakable connecting line;
   wherein the open end of the sheath is spaced apart from the perforated, tearable, and/or breakable connecting line, and the open end is formed from two layers of the sheath presenting a three-dimensional concave opening; and
   wherein the closed end of the sheath is operable to activate a touchscreen of an interactive graphic user interface and a corresponding display upon contact therewith;
   thereby providing protection from contact-based transmission of germs while enabling touchscreen activation that is substantially similar to a direct digit contact with the touchscreen.

13. The protective covering of claim 12, wherein the sheath is formed of a non-porous, impermeable material.

14. The protective covering of claim 12, wherein the sheath is formed of a non-porous, impermeable material that is disposable and biodegradable.

15. The protective covering of claim 12, wherein the sheath is formed of a non-woven material.

16. The protective covering of claim 12, wherein the sheath is formed of a lightweight cellulosic material.

17. The protective covering of claim 16, wherein the sheath is formed of paper.

18. The protective covering of claim 12, wherein the sheath further includes an outer surface and an inner surface, and wherein at least one of the outer surface and inner surface is coated and/or impregnated with a sanitizing agent.

* * * * *